United States Patent [19]

Leibinsohn Saul

[11] 4,449,534
[45] May 22, 1984

[54] LIQUID-FLOW MEASURING DEVICES, PARTICULARLY USEFUL FOR DRIP CHAMBERS

[76] Inventor: Leibinsohn Saul, 11 Oleh Hagardom St., Rishon Lezion, Israel

[21] Appl. No.: 253,801

[22] Filed: Apr. 14, 1981

[30] Foreign Application Priority Data

Apr. 16, 1980 [IL] Israel .................................. 59850
Mar. 10, 1981 [IL] Israel .................................. 62337

[51] Int. Cl.$^3$ .............................................. A61M 5/16
[52] U.S. Cl. .................................... 604/51; 73/861.41
[58] Field of Search ............ 128/214 R, 214 C, 214.2; 73/861.41; 222/420

[56] References Cited

U.S. PATENT DOCUMENTS

| | | | |
|---|---|---|---|
| 3,030,954 | 4/1962 | Thornton | 128/214 C |
| 3,340,871 | 9/1967 | Jellies | 128/214 C |
| 3,826,137 | 7/1974 | Clarke | 128/214 C |
| 4,136,693 | 1/1979 | Dyke | 128/214 C |
| 4,291,693 | 9/1981 | Todd et al. | 128/214 C |

*Primary Examiner*—Dalton L. Truluck
*Attorney, Agent, or Firm*—Benjamin J. Barish

[57] ABSTRACT

A liquid-flow measuring device particularly useful as a drip chamber for infusion administration sets includes a housing having an internal chamber for accumulating the liquid dripping thereinto by gravity introduced via an inlet port which terminates in a first bore leading to a second bore. The housing further includes an air return leading to the juncture of the first and second bores, such that the liquid flowing through the first bore forms a liquid column in the second bore which liquid column grows by gravity until it breaks and drops into the chamber, the length and/or rate the liquid columns grow before passing into the chamber thereby providing a measurement of the rate of flow of the liquid through the device.

11 Claims, 9 Drawing Figures

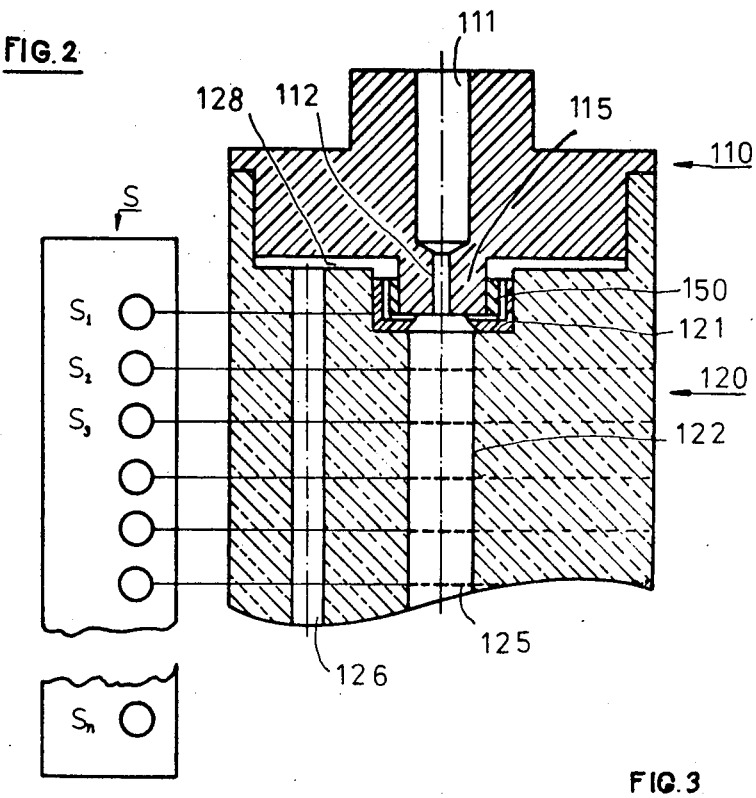
FIG. 2
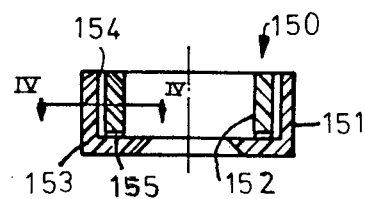
FIG. 3
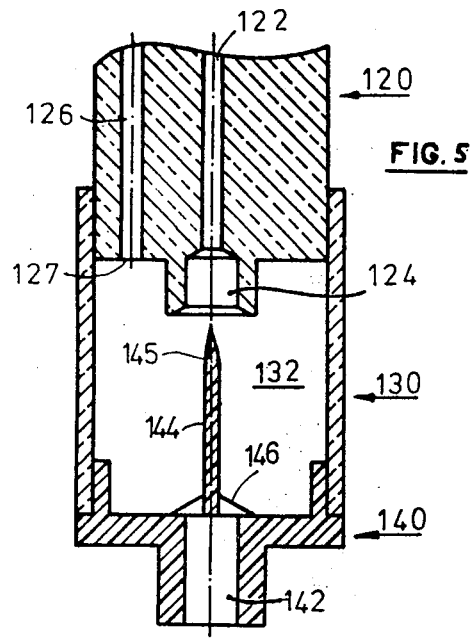
FIG. 5
FIG. 4

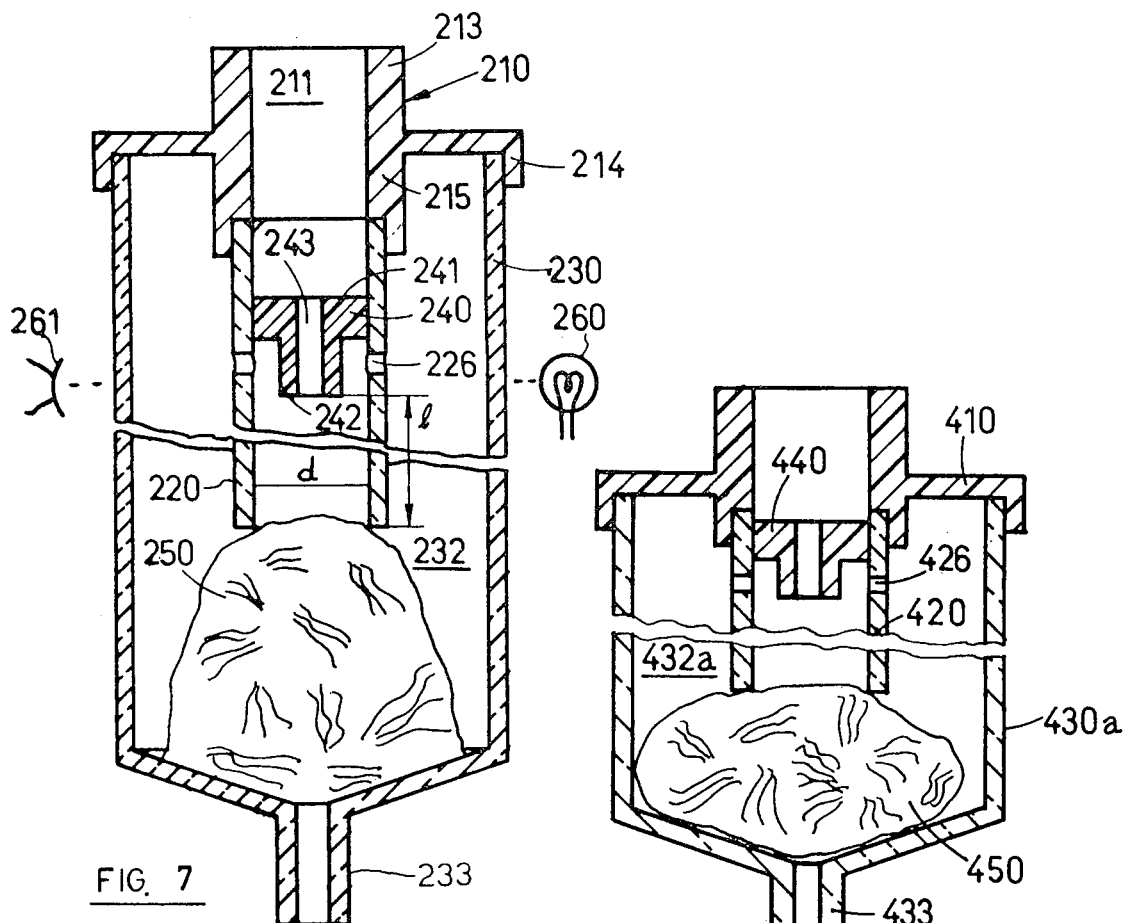
FIG. 7
FIG. 9
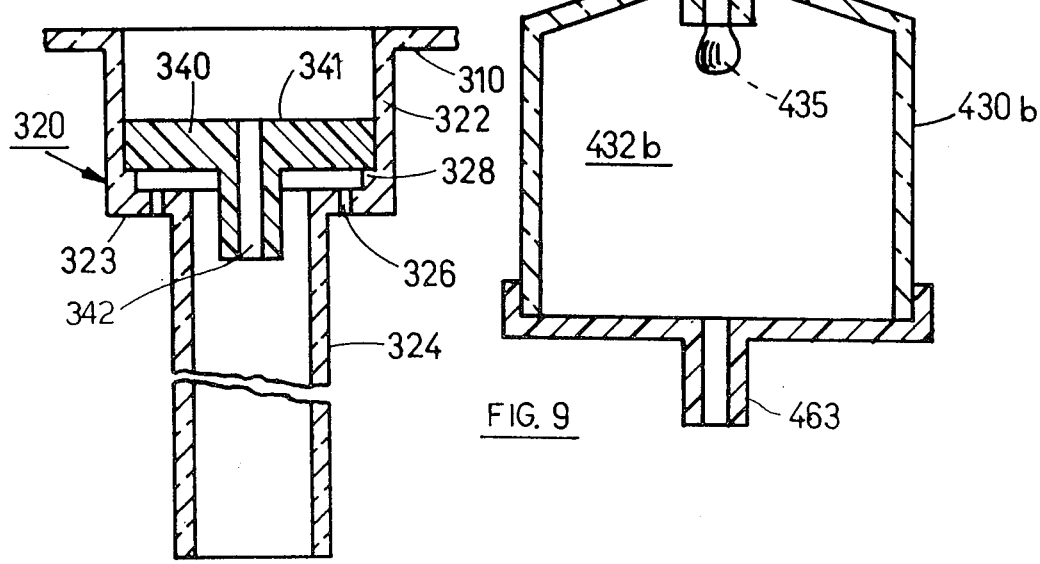
FIG. 8

LIQUID-FLOW MEASURING DEVICES, PARTICULARLY USEFUL FOR DRIP CHAMBERS

BACKGROUND OF THE INVENTION

The present invention relates to liquid-flow measuring devices. The invention is particularly useful in drip chambers for infusion administration sets, and is therefore described below with respect to this application.

Drip chambers for infusion administration sets commonly include a housing having an internal chamber for accumulating the liquid dripping thereinto by gravity introduced via an inlet port at one end, and for feeding the liquid therefrom via an outlet port at the opposite end. Many applications of such drip chambers require the liquid to be administered at a predetermined flow rate and/or for a predetermined quantity. The known arrangements, however, are not very precise with respect to the flow rate or the total quantity of the liquid being administered; moreover they require frequent monitoring by a nurse, thereby adding to her already-heavy workload.

BRIEF SUMMARY OF THE INVENTION

According to a broad aspect of the present invention, there is provided a liquid-flow measuring device particularly useful as a drip chamber for infusion administration sets and including a housing having an internal chamber for accumulating the liquid dripping therein by gravity introduced via an inlet port at one end, and for feeding the liquid therefrom via an outlet port at the opposite end; characterized in that said inlet port terminates in a first bore leading to a second bore, the housing further including an air return leading to the juncture of the first and second bores, such that the liquid flowing through the first bore forms a liquid column in the second bore which liquid column grows downwardly by gravity and breaks away into the chamber before forming a drop at the bottom of the second bore, the length and/or rate said liquid columns grow before breaking away into the chamber thereby providing a measurement of the rate of flow of the liquid through said device.

The invention also provides a method for measuring liquid flow particularly useful in drip chambers for infusion administration sets.

The arrangement may be such that the downwardly growing liquid column in the second bore breaks away before it reaches the bottom of the second bore, so that the length the liquid columns grow in the second bore before breaking away (together with the rate at which they form and break away) provides a measurement of the rate of flow. Alternatively, the device could include a column-breaking element located at the bottom of the second bore so as to be contacted by the liquid column growing therein to cause same to break away when the downwardly-growing liquid column reaches the bottom of the second bore, thereby prefixing the length of the liquid column before passing into the chamber.

In both arrangements, the diameter of the second bore within which the liquid column grows is known, and therefore by monitoring the length of such a column and the rate it breaks away, an accurate measurement may be made of the rate of flow of the liquid through the device.

Further features and advantages of the invention will be described more particularly below.

BRIEF DESCRIPTION OF THE DRAWINGS

The invention is herein described, by way of example only, with reference to the accompanying drawings, wherein:

FIG. 2 is a longitudinal section of the upper end of the device of FIG. 1 but illustrating a modified construction;

FIG. 3 is an enlarged view of a composite sleeve included in the modification of FIG. 2;

FIG. 4 is a fragmentary sectional view along lines IV—IV of FIG. 3;

FIG. 5 is a longitudinal section view of the lower end of the device of FIG. 1 but illustrating a further modification;

FIG. 7 is a longitudinal sectional view illustrating another form of liquid-flow measuring device constructed in accordance with the invention;

FIG. 8 is a fragmentary view illustrating a modification in the device of FIG. 7; and FIG. 9 illustrates a further device constructed in accordance with the invention.

DESCRIPTION OF PREFERRED EMBODIMENTS

Figure 1:
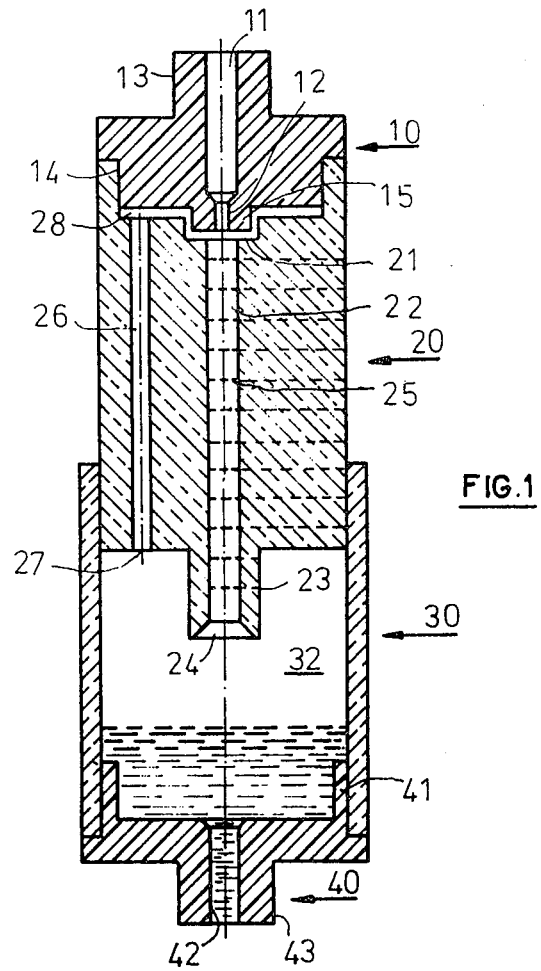
FIG. 1 is a longitudinal sectional view illustrating one form of liquid-flow measuring device constructed in accordance with the invention, the device being embodied in a drip chamber for infusion administration sets.

The liquid-flow measuring device illustrated in FIG. 1 is particularly useful in drip chambers for infusion administration sets. Generally speaking, the device comprises a housing including four main sections attached together, namely a first section 10 including the inlet to the device, a second section 20 including means enabling one to observe the liquid flow such as to provide an indication of the flow rate, a third section 30 defining an internal chamber for accumulating the liquid dripping thereinto by gravity, and a fourth section 40 including an outlet port for feeding the liquid from the latter chamber out of the device. The foregoing parts are of circular cross-section so that the housing is of generally cylindrical configuration. The parts are assembled together by friction fits to facilitate the quick assembly and disassembly of the device.

More particularly, housing section 10 includes the inlet port defined by a longitudinal bore 11 of reduced diameter at its inner end as shown at 12. The outer end of housing section 10 is formed with an external stem 13, preferably tapered, to permit its quick attachment to a flexible tube (not shown), usually of elastomeric (e.g. natural or synthetic rubber) material, leading to the container of the liquid to be administered by the infusion device. The inner end 14 of housing section 10 is similarly tapered for frictional-attachment to housing section 20, and includes a central stem 15 projecting into a corresponding central recess 21 in housing section 20. Bore 12 passes centrally through stem 15.

Housing section 20 is also formed with a central bore 22 extending axially therethrough in alignment with, but of larger diameter than, bore 12. The opposite end of bore 22 passes through a stem 23 projecting below the lower face of housing section 20. The end of bore 22 is enlarged as shown at 24.

Housing section 20 is further provided with a plurality of graduation markings 25 along bore 22, for purposes to be described below. This housing section is further formed with another bore 26 extending axially through the housing section but spaced laterally from central bore 22. Bore 26 does not pass through stem 23, so that the lower end 24 of bore 22 is disposed at a lower elevation than the lower end 27 of bore 26.

Bore 26 serves as an air return passage to the junctures between bores 12 and 22. Thus, the upper end of bore 26 communicates with the juncture between bores 12 and 22 via air passages, which may include an air space 28 between the two housing sections 10 and 20, and/or recesses formed on one or both contacting faces of these housing sections.

Housing section 30 defines an internal chamber 32 with housing sections 20 and 40. Thus, housing section 30 is in the form of a cylindrical sleeve frictionally fittable at one end to the outer surface of housing section 20, and at the opposite end to an axial flange 41 formed in the inner face of housing section 40.

In addition to the attaching flange 41, housing section 40 is formed with a central bore 42 serving as the outlet port for the liquid accumulating within chamber 32, and with a tapered stem 43 for attachment to the infusion line (not shown) leading to the infusion needle.

The relative diameters of bore 12 at the terminal end of the inlet port 11, and bore 22 within housing section 20, are such that the liquid flowing through the inlet port 11 and bore 12 forms a liquid column in bore 22, which liquid column grows until it drops by gravity into chamber 32. Bore 26, and the air passage 28 leading to the juncture of bore 12 with bore 22, provide an air return permitting the liquid column to grow within bore 22 and to drop by gravity into chamber 32. Housing section 20 is of transparent material to permit visual observation, via the graduation markings 25, of the length of the liquid column growing in bore 22. Thus, bore 12 serves as a liquid metering element, and bore 22 serves as a liquid measuring element, enabling the user, by observing the length of the liquid column formed in bore 22 before dropping into chamber 32, and also the rate at which such columns drop into chamber 32, to determine the rate of flow of the liquid through the device.

As one example, for infusion solutions of 0.9% NaCl and 5% or 10% glucose, with the solution source level about 1.20 meters above the patient, the diameter of bore 12 may be about 1.5 mm, and that of bore 22 may be from 2–4 mm (e.g. 3 mm), depending on the flow rate desired.

Since the outlet end 24 of bore 22 is at a lower elevation within the liquid chamber 32 than the inlet end 27 of the air-return bore 26, this decreases the possibility that liquid flowing through bore 22 may clog the inlet end 27 of the air return bore 26. In addition, since the outlet end of bore 12 is formed through stem 15, this decreases the possibility that liquid flowing through bore 12 to form the column growing within bore 22 may clog the air-return passages 28 leading to the juncture between bores 12 and 22, which air return is necessary to permit the liquid column to grow within bore 22 and to drop into chamber 32. In order to further decrease the possibility of clogging the air return path, the outer surface of stem 15, and/or the inner face of the recess 21 receiving same, may be coated with a hydrophobic substance, such as silicone or wax.

FIG. 2 illustrates a modification that may be embodied in the device, particularly at the juncture between the upper housing section therein designated 110, and the adjacent housing section therein designated 120. Thus, in the modification illustrated in FIG. 2, a composite cylindrical sleeve 150 is interposed between stem 115 in housing section 110, and the corresponding recess 121 in housing section 120. Sleeve 150 is of a special construction to provide a non-cloggable air-return passage from bore 126 in housing section 120 to the juncture between bore 112 at the terminal end of the inlet port 111 in housing section 110, and the upper end of bore 122 in housing section 120.

The structure of sleeve 150 is more particularly illustrated in FIGS. 3 and 4, wherein it will be seen that it includes an outer sleeve section 151 coaxially receiving an inner sleeve section 152. The lower end of the outer sleeve section 151 is formed with an apertured end wall 153 engaged by the lower face of the inner sleeve section 152. In addition, the outer face of sleeve section 152 is formed with a plurality of axially-extending, circumferentially-spaced recesses 154 leading to radially-extending recesses 155 formed in the lower face of sleeve section 152.

As shown particularly in FIG. 2, the lower end of stem 115 in housing section 110 seats against the inner face of the apertured end wall 153 of sleeve section 151 such as to provide a space 128 between the confronting lower face of housing section 110 and upper face of housing section 120. This space 128 is in the air-return path from bore 126, which path also includes recesses 154 and 155 in the composite sleeve 150 leading to the juncture between bore 112 in housing section 110, and bore 122 in housing section 120. This air-return path thus permits the liquid flowing through bore 112 to form a growing column within bore 122, as described above with respect to FIG. 1, without danger of clogging.

FIG. 5 illustrates a modification that may be provided at the lower end of the device illustrated in FIG. 2 to further assure that the liquid exiting from the column-measuring bore 122 into chamber 132, formed by housing section 130, will not clog the air inlet opening 127 of the air-return duct path 126. For this purpose, the lower housing section 140 with the outlet port 142 is provided with a vertical stem 144 having a pointed upper end 145 in alignment with the outlet end 124 of bore 122, in order to break or pierce any drop forming at the lower end, and thereby to prevent same from covering or clogging the inlet end 127 of the air-return path 126. Stem 144 is preferably integrally formed with housing section 144 by means of a plurality of spaced radially-extending ribs 146 to provide a passage for the fluid flow from chamber 132 through the outlet port 142.

As described above with respect to FIG. 1, housing section 120 may be formed with a plurality of graduation markings 125 along bore 122 to permit visual observation of the length of the liquid column growing within the bore before dropping into the drip chamber. Thus, by visually observing the length of the vertical column in bore 122 before it drops into the chamber, and the rate at which such vertical columns drop into the chamber, one may easily determine the rate of flow of the liquid through the device. In practice, it would normally be necessary to make the above observations only with respect to the first few drops, since the column length and drop rate will generally remain substantially constant for the complete procedure. The user may therefore be provided with a chart or table converting column length and drop rate to rate of flow per unit time.

For a more precise measurement of the flow rate, the device may be provided with an electrical measuring circuit comprising a sensor circuit S including a plurality of sensors $S_1, S_2 \ldots S_n$, each sensor optically aligned with one of the graduation markings 125 along the length of bore 122 as shown in FIG. 2. Thus, the first sensor $S_1$ would be aligned with the juncture line between the lower end of bore 112 and the upper end of bore 122. This sensor can be used to indicate when the liquid column growing within bore 122 drops into the drip chamber since, at this instant, it will sense an interruption in the liquid at this juncture line. The rate of such interruptions would thus indicate the rate at which the drops fall into the drip chamber. In addition, the sensor circuit S may be designed so that as soon as this interruption by sensor $S_1$ is sensed, the length of the column can be determined, by sensing where its bottom edge lies with respect to the remaining sensors. Optical sensors and circuits which may be used for this purpose are known in the art, for example, in optical character or pattern recognition systems, and therefore further details of the construction or operation of such sensors are not deemed necessary herein.

Figure 6:
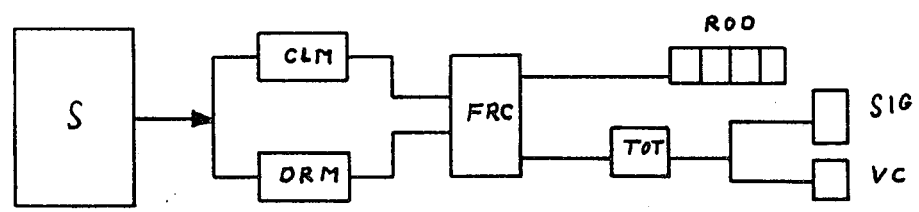
FIG. 6 is a block diagram of an electrical measuring circuit that may be used with the illustrated device.

The complete electrical measuring circuit is schematically shown in block diagram form in FIG. 6, wherein it will be seen that the sensors of circuit S are connected to a column-length-measuring circuit CLM and to a drop-rate-measuring circuit DRM. The latter two circuits are connected to a flow-rate calculator FRC which calculates the flow rate from the information received from circuits CLM and DRM. The flow-rate calculator FRC outputs its readings to a read-out display ROD to provide a continuous display of the flow-rate, namely the flow quantity e.g., ml/min. The flow-rate calculator FRC may be also connected to a totalizer TOT which may be preset for a predetermined quantity, so as to control a signalling device SIG providing a signal (visual or audio) when the predetermined quantity has been reached, and/or a valve control circuit VC to terminate the infusion procedure when the predetermined quantity has been reached.

FIGS. 7–9 illustrate further devices constructed in accordance with the invention wherein the device includes a column-breaking element located so as to be contacted by the growing liquid column, and to break same, slightly before the liquid column would otherwise break by gravity alone. Such an arrangement thereby prefixes the length of the liquid column before breaking and passing into the drip chamber, so that it is only necessary to count the rate such breakages occur in order to determine the rate of liquid flow.

The device illustrated in FIG. 7 comprises three main sections, designated 210, 220, and 230, respectively. Section 210 is formed with a bore 211, an external stem 213, an annular flange 214, and an internal stem 215. The external stem 213 is adapted to receive the connecting flexible tube through which the administered liquid is fed. Annular flange 214 receives, e.g. by a press-fit, section 230 of generally cylindrical configuration to define a cylindrical housing having an internal chamber 232 for the administered liquid, the opposite end of the housing being formed with an external stem 233 to be connected to the tube outletting the administered liquid. Internal stem 215 of section 210 receives, e.g., also by a friction fit, section 220 which is in the form of a hollow sleeve through which the administered liquid flows into chamber 232.

Hollow sleeve 220 is formed with one or more (e.g. a circular array) of openings 226 near its upper end. An apertured member 240, of hydrophobic material non-wettable by the administered liquid, is received in the upper end of the hollow sleeve 220 above openings 226. The hydrophobic member 240 is formed with an enlarged head 241 press-fitted against the inner face of hollow sleeve 220, and with a depending stem 242 of smaller diameter than its head 241, the arrangement being such that stem 242 is spaced radially inwardly of the inner face of sleeve 220 through which the openings 226 are formed and depends below these openings. A bore 243 is formed through both the enlarged head 241 and the depending stem 242 of the hydrophobic member 240.

Bore 243 through the hydrophobic member 240 is of smaller diameter than bore 211 of the inlet to the chamber and acts as the metering bore for metering the liquid. The hollow sleeve 220 acts as the column-growing bore in which the liquid column grows by gravity, and openings 226 through sleeve 220 act as the air-return passages at the juncture of the two bores to permit the liquid column to grow within sleeve 220 until the liquid column would normally drop by gravity into chamber 232.

In the arrangement illustrated in FIG. 7, however, sleeve 220 is not of such length as to permit the liquid column to break off by gravity alone and to drop into chamber 232. Instead, the device includes a column-breaking element located so as to be contacted by the liquid column growing within sleeve 220 and to break same slightly before the liquid column would otherwise break by gravity alone. This arrangement thereby prefixes the length of the liquid column before dripping into chamber 232, so that by knowing the dimensions (length and diameter) of hollow sleeve 220 below the bottom of the apertured hydrophobic member 240, one may easily make a determination of the flow rate of the liquid through the device by merely counting the rate at which the liquid column breaks within sleeve 220.

In the arrangement illustrated in FIG. 7, the column-breaking element is in the form of a liquid absorbent material, such as a plastic mesh, e.g. "Dacron" (Reg. TM ), a sponge, or a filtering material. This element is disposed within chamber 232 with its upper face engaging the bottom face of the hollow sleeve 220 so as to be contacted by the liquid column growing within the sleeve as soon as it reaches it. When this occurs, the liquid within the sleeve is absorbed by the mesh 250 to break the liquid column growing within sleeve 220, whereupon a new liquid column begins to form.

Thus, by noting, visually or optically, e.g. by the use of an aligned light source 260 and photocell 261 disposed just below the hydrophobic apertured member 240, the rate at which the liquid column breaks, one can determine the rate of flow of the liquid through the device.

As one example, for infusing solutions of 0.9% NaCl and 5% or 10% glucose, with a solution source level about 1.20 meters above the patient, bore 243 may be about 2 mm diameter, hollow sleeve 220 may be 3.15 mm inner diameter (d), and the length (l) of the sleeve 220 from the bottom face of member 240 to the upper face of the mesh 250 may be about 15 mm. This produces about 8 drop/ml. In the above example, the inner diameter (d) may vary from about 2.0 mm to about 3.8 mm to change the size of the drops, i.e. the number of drops/ml.

In the above-described example, sleeve 220 may be clear polyvinyl chloride, and the hydrophobic apertured member 240 may be propylene or polytetrafluoroethylene. Member 240 may be integrally formed with the hollow sleeve 220, in which case the material should be a clear hydrophobic material, such as polypropylene.

FIG. 8 illustrates a modification in the FIG. 7 construction, wherein the upper housing section, therein designated 310, is integrally formed with the hollow sleeve, therein designated 320. This can be conveniently achieved, e.g. by injection molding. In this construction, the hollow sleeve 320 is enlarged at its upper end 322, and its annular juncture 323 with its lower end 324 of the sleeve is formed with the air-return openings 326. In addition, the apertured hydrophobic member 340 is applied to the upper, enlarged-diameter end 322 of sleeve 320, by press-fitting the member against an inner annular rib 328, so as to space the bottom face of the member's head 341, and also its depending stem 342, from the air-return openings 326.

The construction illustrated in FIG. 8 is used within a cylindrical housing section (not shown) corresponding to housing section 230 in FIG. 7, and otherwise operates in the same manner as described above with respect to FIG. 7.

In the embodiment illustrated in FIGS. 7 and 8, the observer actually does not see drops forming within the drip chamber, since the complete formation of the drops is terminated by the contact of the liquid with absorbent material (250, FIG. 7). In some applications it would be desirable to permit the observer to actually see the drops being formed, so that the operation will more closely resemble the usual operation of drip chambers. In such applications, the arrangement illustrated in FIG. 9 may be used.

The FIG. 9 arrangement includes two drip chambers, one of which is used for measuring the rate of flow of the liquid, and the other of which is used for forming drops which may be observed. Thus, the cylindrical housing in FIG. 9 is constituted of two sections, namely an upper section 430a defining an upper chamber 432a, and a lower section 430b defining a lower chamber 432b. The upper section 430a is constructed in the same manner as described above, e.g., in FIG. 7, for measuring the rate of flow of the liquid, this section including the hollow sleeve 420 for forming the liquid columns, the hydrophobic metering member 440 at the upper end of the sleeve, the air-return openings 426 through the sleeve, and the column-breaking absorbent mesh, sponge or filter 450 in contact with the lower end of the sleeve. The liquid thus accumulating in the upper chamber 432a flows through its outlet 433 into the lower chamber 432b defined by the lower housing section 430b. As this liquid flows from chamber 432a into chamber 432b, it forms distinct observable drops, as shown at 435, before falling by gravity into chamber 432b from which it is outletted via outlet 463 to the patient. It will be appreciated, however, that whereas the liquid is inletted into the lower chamber 432b in the form of observable drops 435, the rate of formation of these drops is not what indicates the rate of flow of the liquid, but rather the rate of breakage of the liquid column within the hollow sleeve 420, as described above, is what provides the indication of the liquid flow rate.

Many other variations in the above-described embodiments of the invention may be made. For example, the invention may also advantageously be used in arrangements wherein there is no air-return leading to the juncture of the metering bore (e.g. 243, FIG. 1) with the measuring bore (e.g. sleeve 220, FIG. 1), so that the liquid does not form a column growing by gravity within the latter bore, but rather forms a drop at the outlet end of the bore leading into the drip chamber. In such an application, the liquid absorbent material may be spaced from the outlet end of the latter bore a distance which is less than the diameter of the drop which would otherwise normally form before breaking by gravity, whereby the liquid absorbent material also prefixes the size, or volume, of the liquid (being a drop in this case, rather than a column) before passing into the chamber. In such an arrangement, by observing the rate of breakage of each of the liquid drops, there is provided a measurement of the rate of feed of the liquid.

What is claimed is:

1. A liquid-flow measuring device particularly useful as a drip chamber for infusion administration sets and including a housing having an internal chamber for accumulating the liquid dripping thereinto by gravity introduced via an inlet port at one end, and for feeding the liquid therefrom via an outlet port at the opposite end; characterized in that said inlet port terminates in a first bore leading to a second bore at a juncture between the two bores, the housing further including an air passage leading to said juncture of the first and second bores, such that the liquid flowing through said first bore forms a liquid column in said second bore which liquid column grows downwardly by gravity and breaks away into said chamber before forming a drop at the bottom of said second bore, the length and/or rate said liquid columns grow before breaking away into the chamber thereby providing a measurement of the rate of flow of the liquid through said device.

2. A device according to claim 1, wherein at least the portion of the housing containing said second bore is transparent and is provided with graduation markings along the length of said second bore to permit the length of the liquid column growing therein to be visually observed.

3. The device according to claim 1, wherein said device further includes a column-breaking element located at the bottom of said second bore so as to be contacted by the liquid coulmn growing in said second bore, and to break same, when said downwardly-growing liquid column reaches the bottom of said second bore, to thereby prefix the length of said liquid column before passing into said chamber.

4. The device according to claim 3, wherein said column-breaking element is a liquid-absorbent element which is contacted by the liquid column to break same.

5. The device according to claim 3, wherein said column-breaking element is a pointed stem disposed in said chamber such as to be contacted by the liquid column when it reaches the lower end of said second bore.

6. The device according to claim 1, wherein said second bore is defined by a hollow sleeve whose lower end is disposed within said chamber, the upper end of said hollow sleeve being formed with openings therethrough to define said air-return leading to the juncture of said first and second bores.

7. The device according to claim 6, further including an axially-apertured hydrophobic member defining said first bore, said hydrophobic member being disposed above said air-return openings to prevent clogging thereof by liquid passing through said first bore.

8. The device according to claim 6, wherein said device further includes a column-breaking element located at the bottom of said second bore so as to be contacted by the liquid column growing in said hollow sleeve to break same when said downwardly-growing liquid column reaches the bottom of said second bore, to thereby prefix the length of said liquid column before passing into said chamber.

9. A method for measuring liquid flow particularly in a drip chamber for infusion administration sets including a housing having an internal chamber for accumulating the liquid dripping thereinto by gravity introduced via an inlet port at one end, and for feeding the liquid therefrom via an outlet port at the opposite end; characterized in feeding the liquid from a first bore in said housing into a second bore in said housing, which housing has an air passage leading to the juncture of the first and second bores, the diameter of the second bore being sufficiently large such as to form a liquid column in the second bore which liquid column grows downwardly by gravity and breaks away into the chamber before forming a drop at the bottom of the second bore; and monitoring the length and/or the rate the liquid columns grow in said second bore before breaking away, to provide a measurement of the rate of flow of the liquid through the device.

10. The method according to claim 9, wherein the liquid column growing downwardly by gravity in said second bore breaks away before the liquid column reaches the bottom of the second bore.

11. The method according to claim 9, wherein a column-breaking element is provided at the bottom of the second bore so as to be contacted by the liquid column growing downwardly in the second bore when it reaches the bottom thereof.

* * * * *

UNITED STATES PATENT AND TRADEMARK OFFICE
CERTIFICATE OF CORRECTION

PATENT NO. : 4,449,534
DATED : May 22, 1984
INVENTOR(S) : Saul Leibinsohn

It is certified that error appears in the above-identified patent and that said Letters Patent is hereby corrected as shown below:

Column 7, line 3, change "propylene to -- polypropylene --.
Column 8, line 27, in Claim 1, line 11, after "bores" and before "such that" insert --the diameter of said second bore being sufficiently larger --.

Signed and Sealed this

Twentieth Day of January, 1987

Attest:

DONALD J. QUIGG

*Attesting Officer*   *Commissioner of Patents and Trademarks*